(12) United States Patent  
Kent

(10) Patent No.: US 12,090,609 B2  
(45) Date of Patent: Sep. 17, 2024

(54) TORQUE WRENCH MECHANISM

(71) Applicant: DEPUY SYNTHES PRODUCTS, INC., Raynham, MA (US)

(72) Inventor: Todd J. Kent, Cherry Hill, NJ (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/936,271

(22) Filed: Sep. 28, 2022

(65) Prior Publication Data  
US 2024/0100661 A1 Mar. 28, 2024

(51) Int. Cl.  
*B25B 23/142* (2006.01)  
*B25B 23/14* (2006.01)  
*A61B 17/88* (2006.01)

(52) U.S. Cl.  
CPC ........ *B25B 23/1427* (2013.01); *B25B 23/141* (2013.01); *A61B 17/8875* (2013.01)

(58) Field of Classification Search  
CPC . B25B 23/1427; B25B 23/141; B25B 23/142; B25B 13/465; A61B 17/8875  
USPC .......................................................... 81/477  
See application file for complete search history.

(56) References Cited

U.S. PATENT DOCUMENTS

| | | | |
|---|---|---|---|
| 2,250,941 A * | 7/1941 | Zimmerman | B25B 23/1427 267/128 |
| 2,300,652 A | 11/1942 | Cooney | |
| 2,358,461 A * | 9/1944 | Latimer | B25B 23/1427 81/60 |
| 2,400,205 A | 5/1946 | Livermont | |
| 2,407,450 A | 9/1946 | Reilly et al. | |
| 2,764,272 A | 9/1956 | Reynolds | |
| 2,765,890 A | 10/1956 | Pedersen et al. | |
| 3,456,486 A | 7/1969 | Kross | |
| 3,525,256 A | 8/1970 | Crooks et al. | |
| 3,577,778 A | 5/1971 | Liepins | |
| 4,558,601 A | 12/1985 | Stasiek et al. | |
| 4,643,030 A | 2/1987 | Becker et al. | |
| 4,665,756 A | 5/1987 | Snyder | |
| 5,345,845 A | 9/1994 | Myers | |
| 5,848,655 A | 12/1998 | Cooper et al. | |
| 7,021,180 B2 | 4/2006 | Crane | |
| 7,159,494 B2 | 1/2007 | Jamnia et al. | |
| 8,359,099 B2 | 1/2013 | Lim | |

(Continued)

*Primary Examiner* — Eric J Rosen  
*Assistant Examiner* — Robert C Moore  
(74) *Attorney, Agent, or Firm* — Fay Kaplun & Marcin, LLP

(57) ABSTRACT

A torque wrench includes an elongated body, a head, and a cantilever beam. The body extends longitudinally from a proximal end to a distal end and includes a channel extending therethrough. The distal end includes an opening extending laterally therethrough along a central axis. The head is rotatably received within the opening at the distal end so that the head is rotatable about the axis. The head includes a gear cam defining teeth about a periphery thereof and an engaging portion sized, shaped, and configured to engage a corresponding engaging feature of a fixation device. The beam is housed within the channel such that a distal tip is received in a space between adjacent teeth. The beam bends when a torsional force applied to the head exceeds a predetermined limit so that the cam rotates about the axis and the distal tip slips from the space between the teeth into an adjacent space.

12 Claims, 5 Drawing Sheets

(56) References Cited

U.S. PATENT DOCUMENTS

| | | |
|---|---|---|
| 8,435,258 B2 | 5/2013 | Young et al. |
| 9,023,072 B2 | 5/2015 | Young et al. |
| 11,103,984 B2 | 8/2021 | Kuo |
| 11,266,432 B2 | 3/2022 | Brown et al. |
| 2011/0154961 A1* | 6/2011 | Kan ..................... B25B 13/465 81/478 |
| 2016/0075005 A1* | 3/2016 | Hayes, Jr. ............. B25B 23/142 81/186 |
| 2022/0250219 A1* | 8/2022 | Anjanappa .......... B25B 23/1427 |

* cited by examiner

TORQUE WRENCH MECHANISM

BACKGROUND

Torque wrenches are used in a variety of applications to apply a specific torque to, for example, a fixation device such as a nut, bolt, or screw, etc. The torque wrench allows the user to set the torque applied to the fixation device so that it may be matched to the specifications of a particular application, permitting proper tension and loading of all parts. Many current torque wrenches use Belville washers/springs or a cam disk for creating the torque limit. Some mechanical torque wrenches rely on a bending of a handle of the wrench.

SUMMARY OF THE INVENTION

The present disclosure relates to a torque wrench which includes an elongated body extending longitudinally from a proximal end to a distal end and including a channel extending therethrough. The distal end includes an opening extending laterally therethrough along a central axis. The opening and the channel are in communication with one another. The wrench also includes a wrench head rotatably received within the opening at the distal end of the elongated body so that the wrench head is rotatable about the central axis. The wrench head includes a gear cam defining a plurality of teeth about a periphery thereof and an engaging portion sized, shaped, and configured to engage a corresponding engaging feature of a fixation device to which a torsional force is to be applied via the torque wrench. In addition, the wrench includes a cantilever beam housed within the channel of the elongated body such that a distal tip thereof is received in a space between adjacent teeth of the gear cam, the cantilever beam configured to bend when a torsional force applied to the wrench head exceeds a predetermined torque limit so that the gear cam rotates about the central axis and the distal tip slips from the space between the teeth into an adjacent space.

In an embodiment, the torque wrench further includes a torque adjuster extending about a portion of the cantilever beam and slidable along the elongated body to set a bendable length of the cantilever beam and adjust a desired torque limit of the torque wrench.

In an embodiment, the bendable length is defined via a portion of the cantilever beam extending distally of the torque adjuster.

In an embodiment, the torque adjuster configured as a slidable tab biased toward a locked configuration, in which the tab is fixed in a position along the elongated body, and an unlocked configuration, in which the tab is slidable along the elongated body.

In an embodiment, the torque wrench further includes a set beam extending proximally from a proximal end of the cantilever beam in longitudinal alignment therewith, the set beam configured to engage a proximal portion of the channel of the elongated body to fix a position of the cantilever beam within the elongated body.

In an embodiment, the set beam including a threading extending therealong.

In an embodiment, the torque wrench further includes a nut mounted within the proximal portion of the channel, the nut configured to threadedly engage the threading of the set beam.

In addition, the present disclosure relates to a device for exerting a torsional force to a fixation device. The device includes a body extending along a longitudinal axis from a proximal end to a distal end and including a channel extending therethrough along the longitudinal axis. The distal end includes an opening extending laterally therethrough along a central axis. The device also includes a wrench head rotatably mounted within the opening such that the wrench head is rotatable about the central axis. The wrench head includes a gear cam including teeth about a periphery thereof and an engaging portion configuration to engage a fixation device. In addition, the device includes a cantilever beam extending through the channel so that a distal tip thereof is received between adjacent teeth of the gear cam. The cantilever beam is configured to bend when a torsional force applied to the wrench head exceeds a predetermined torque limit so that the distal tip slips from between the adjacent teeth. Furthermore, the device includes a torque adjuster slidable along the body to set a desired bendable length of the cantilever beam and adjust a desired torque limit of the wrench head.

In an embodiment, the torque adjuster includes a tab extending about a portion of the cantilever beam so that the tab is slidable along a length thereof.

In an embodiment, the tab is configured to be movable between a locked configuration, in which the tab is in a fixed position along the body, and an unlocked configuration, in which the tab is slidable along the body.

In an embodiment, the device further includes a set beam extending proximally from a proximal end of the cantilever beam to engage a portion of the channel.

In an embodiment, the set beam includes a threading extending thereabout and along a length thereof.

In an embodiment, a proximal portion of the channel of the body includes a nut mounted therein, the nut configured to threadedly engage the set beam therein.

In addition, the present disclosure relates to a method for applying a torsional force to a fixation device. The method includes engaging an engaging element of a wrench head of a torque wrench with a corresponding engaging portion of the fixation device, the torque wrench including an elongated body, a gear cam of the wrench head rotatably mounted within an opening at a distal end of the elongated body, a cantilever beam extending through the elongated body so that a distal tip of the cantilever beam is received in a space between adjacent teeth of the gear cam; and applying a torsional force to the fixation device by rotating the elongated body about a central axis of the wrench head until a torque limit is reached. When the torque limit is reached, the cantilever beam bends such that the gear cam rotates about the central axis and the distal tip of the cantilever beam slips from between the adjacent teeth so that no further torsional force is applied to the fixation device.

In an embodiment, the method further includes adjusting a torque limit of the torque wrench.

In an embodiment, the torque limit is adjusted by sliding a torque adjuster along a length of the elongated body and the cantilever beam to define a bendable length of the cantilever beam.

In an embodiment, the torque limit is adjusted by adjusting a position of the cantilever beam relative to the elongated body.

In an embodiment, the position of the cantilever beam is adjusted via a set beam which extends proximally from a proximal end of the cantilever beam to engage a portion of a channel of the elongated body.

In an embodiment, a proximal portion of the channel includes a nut mounted therein and the set beam includes a threading extending therealong for threadedly engaging the nut.

BRIEF DESCRIPTION

DETAILED DESCRIPTION

Figure 1:
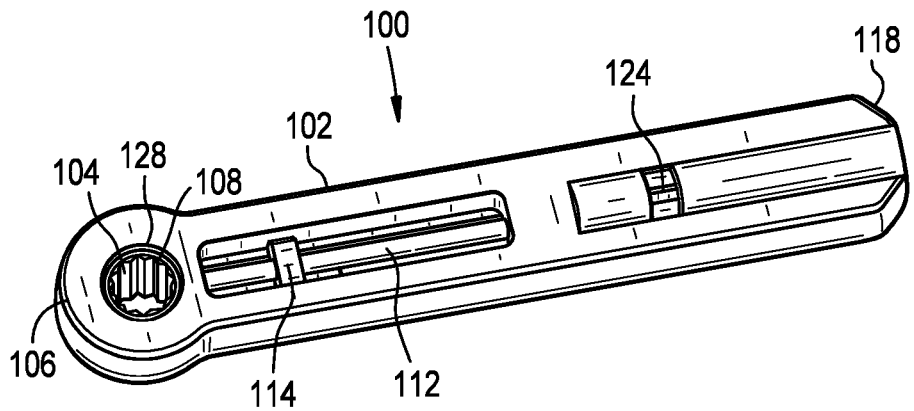
FIG. 1 shows a perspective view of a torque wrench according to an exemplary embodiment of the present disclosure.

The present disclosure may be further understood with reference to the following description and the appended drawings, wherein like elements are referred to with the same reference numerals. The present disclosure relates to torque wrenches and, in particular, relates to various torque wrench mechanisms for setting desired torque limits. Exemplary embodiments of the present disclosure describe a torque wrench including a cantilever beam that may be adjusted to set a desired torque limit. Although the exemplary embodiments included herein describe torque wrenches that are used to manipulate bone fixation devices (e.g., bone screws), those skilled in the art will understand that torque wrenches constructed as described herein may be used in any application in which it is desired to apply a known torque to any item—i.e., any application in which conventional torque wrenches are applied. In an exemplary embodiment of the present disclosure, a torque wrench includes a torque indicator providing tactile feedback to an operator of the wrench when a torque limit has been reached. It will also be understood by those of skill in the art that the terms proximal and distal, as used herein, are intended to refer to a direction toward (proximal) and away from (distal) an operator or user of the torque wrench.

Figure 2:
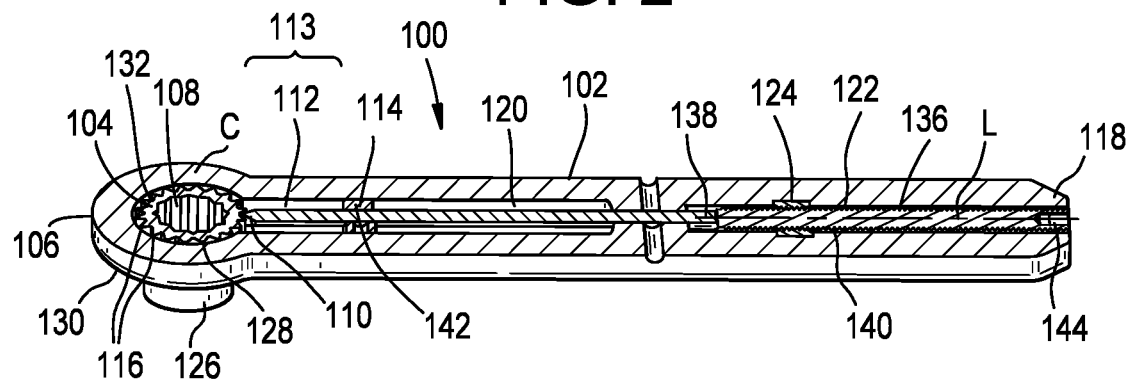
FIG. 2 shows a longitudinal cross-sectional perspective view of the torque wrench of FIG. 1.
Figure 3:
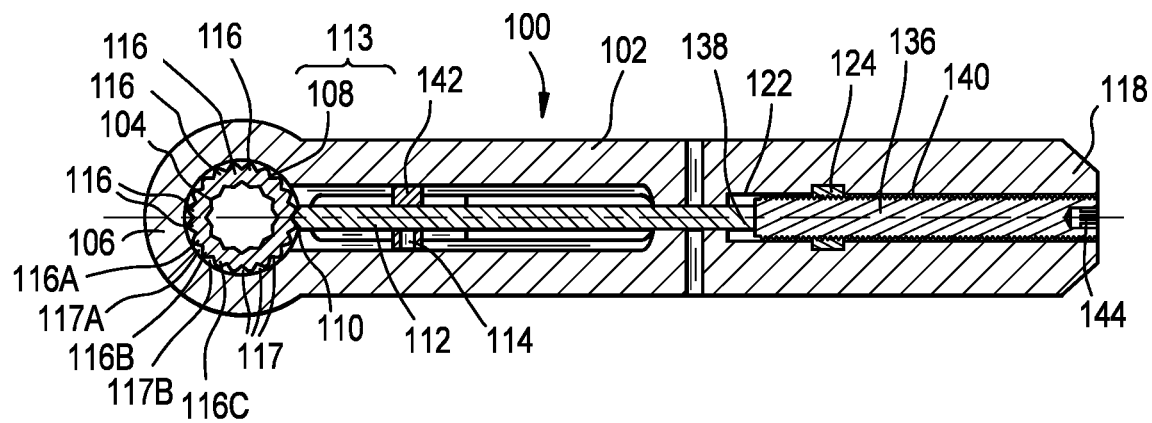
FIG. 3 shows a longitudinal cross-sectional view of the torque wrench of FIG. 1.

FIGS. 1-3 show a torque wrench 100 for applying a desired torque to a fixation device and, in particular, to a bone fixation device according to an exemplary embodiment. The torque wrench 100 comprises a longitudinally extending body 102 including a wrench head 104 rotatably received within a distal end 106 of the body 102. An outer circumference of the wrench head is formed as a gear cam 108 configured to engage a distal tip 110 of a cantilever beam 112, which extends longitudinally through the body 102. The torque wrench 100 also includes a torque adjuster 114 which, in an exemplary embodiment, is configured as a tab that is slidably movable longitudinally along the body 102.

The torque adjuster 114 extends about and laterally stabilizes the part of the cantilever beam 112 extending within the torque adjuster 114 so that adjusting the position of the torque adjuster 114 along the length of the body 102, alters a length of a portion of the cantilever beam 112 that is free to bend (e.g., a bending portion 113) as torsional force applied to the wrench head 104 is applied to the bending portion 113 via the gear cam 108. The bending portion 113 of the cantilever beam 112 of this embodiment extends distally from a distal end of the torque adjuster 14 to the distal end of the cantilever beam 112. The length of the bending portion 113 is adjustable by the user by varying a position of the torque adjuster 14 along the cantilever beam 112 to select a length of the bending portion 113 corresponding to a desired torque limit. In use, a portion of the wrench head 104 engages a fixation device (e.g., a bone fixation device such as a bone screw) so that rotation of the torque wrench 100 about a central axis of the wrench head 104 is applied to the gear cam 108 and, consequently, to a fixation device received therein as the distal tip 110 of the cantilever beam 112 is provisionally locked between a first pair of adjacent teeth 116 of the gear cam 108.

When the torque applied to the torque wrench 100 reaches the desired torque limit, the distal tip 110 of the cantilever beam 112 is bent until it slips from between the first pair of adjacent teeth 116 so that the wrench head 104 rotates until the distal tip 110 comes to rest between a second pair of adjacent teeth 116 again provisionally rotationally locking the position of the wrench head 104 until the torque applied thereto again exceeds the torque limit. Thus, by selecting the length of the bending portion 113 via the positioning of the torque adjuster 114, the user sets a maximum level of torque that can be applied by the torque wrench 100 to a fixation device. That is, when the torque limit is reached, the cantilever beam 112 is bent so that the distal tip 110 slips from between the adjacent teeth 116 the gear cam 108 to another space between an adjacent set of teeth so that the gear cam 108 will no longer rotate a fixation device inserted therein, preventing the application of torsional force beyond the torque limit set by the user.

As would be understood by those skilled in the art, knowing the rigidity of the cantilever beam 112, the geometry of the teeth 116, the torque limit corresponding to a given length of the bending portion 113 may be determined. Alternatively, the torque limits corresponding to various positions of the torque adjuster 114 may be determined by applying known levels of torque to the gear cam 108 and adjusting the position of the torque adjuster 114 to a maximum length of the bending portion 113 at which the distal tip 110 remains positioned between the first pair of teeth 116 without slipping under each torque level. The torque limits corresponding the various positions of the torque adjuster may then be marked on the body 102.

The body 102 of the torque wrench 100 extends longitudinally from a proximal end 118 to the distal end 106. The body 102 is elongated and generally ergonomically shaped and configured such that a user of the torque wrench 100 may grip the torque wrench 100 via, for example, a proximal portion of the body 102. The distal end 106 is sized, shaped, and configured to rotatably receive the wrench head 104 therein. In an exemplary embodiment, the distal end 106 includes an opening 128 extending laterally therethrough along a central axis C. A length of the body 102 proximal of the wrench head 104 includes a channel 120 extending therethrough along a longitudinal axis L, the channel 120 is configured to receive the cantilever beam 112 therein. The channel 120 is in communication with the opening 128. In an exemplary embodiment, the longitudinal axis L along which the channel 120 extends is substantially perpendicular to the central axis C along which the opening 128 extends.

According to an exemplary embodiment, a proximal portion 122 of the channel 120 includes a nut 124 mounted therein, the nut 124 configured to threadedly engage a set beam 136 at a proximal end 138 of the cantilever beam 112, as will be described in further detail below. Although the exemplary embodiments show and describe a nut 124, it will be understood by those of skill in the art that the body 102 may include any of a variety of other mechanisms for holding and/or engaging the set beam 136.

The wrench head 104 is formed as a substantially cylindrical body including the gear cam 108 formed on a radially outer surface thereof and an engaging portion 126 including a central opening sized, shaped, and configured to non-rotatably engage an engaging portion of the bone fixation device (e.g., where a shape of the central opening of the engaging portion 126 is keyed to a peripheral shape of the bone fixation device so the bone fixation device is not rotatable within the engaging portion 126). The gear cam 108 is rotatably mounted within the opening 128 at the distal end 106 of the body 102 so that the wrench head 104 is rotatable relative to the body 102 about the central axis C when not lockingly engaged by the cantilever beam 112.

In an exemplary embodiment, the gear cam 108 has a circular cross-section that is substantially circular (where radially outer-most points of the gear teeth 116 are located equidistant from a central point, i.e., on a circle) sized and shaped to be received within a correspondingly shaped circular opening 128. The gear cam 108 includes a plurality of teeth 116 (e.g., a first tooth 116A, a second tooth 116B, and a third tooth 116C) distributed about a periphery 132 (e.g., circumference) thereof and a plurality of spaces 117 (e.g., a first space 117A and a second space 117B) between the teeth 116, so that, when the gear cam 108 is received within the opening 128, the teeth 116 extend toward an interior surface 134 defining the opening 128 but separated therefrom by a clearance permitting rotation of the gear cam 108 within the opening 128. It will be understood by those of skill in the art that the teeth 116 of this embodiment are consistently sized and shaped and include outer-most points that are equidistantly spaced from one another so that the distal tip 110 may be received between any two adjacent teeth 116.

The engaging portion 126 extends from opening 128 so that the engaging portion 126 extends laterally beyond an exterior surface 130 of the body 102 (along the central axis C) to engage a bone fixation device such as, for example, a nut, bolt, or screw. The engaging portion 126 is sized, shaped, and configured to engage a corresponding engaging portion of the bone fixation device to be applied. In one embodiment, as shown in FIG. 2, the engaging portion 126 is configured as a socket including a recess sized, shaped, and configured to non-rotatably engage an exterior surface of a fixation device such as, for example, a nut a bolt. For example, the engaging portion 126 in this embodiment includes a hex-shaped recess corresponding to an exterior hex-shaped surface of a nut.

In another embodiment, the engaging portion 126 is shaped to correspond to an engaging recess of a screw. For example, an exterior of the engaging portion 126 according to such an embodiment is hex-shaped or star-shaped to correspond to the shape of the recess of a screw. It will be understood by those of skill in the art, however, that the engaging portion 126 may have any of a variety of shapes and configurations so long as the engaging portion 126 is sized, shaped, and configured to correspond to and non-rotatably engage an engaging portion of the bone fixation device to which the torsional force is to be applied.

The cantilever beam 112 of this embodiment is configured as a rod extending longitudinally from the proximal end 138 to the distal tip 110. The distal tip 110 is configured to be received in a space 117 extending between adjacent teeth 116 of the gear cam 108. The cantilever beam 112 is sized, shaped, and configured to be longitudinally movably received within the channel 120 of the body 102. As discussed above, the set beam 136 is non-rotatably coupled to the proximal end 138 of the cantilever beam 112 and is coaxially aligned therewith so that the set beam 136 is received within the proximal portion 122 of the channel 120. The set beam 136 includes threading 140 extending thereabout and along a length thereof or along at least a portion of the length thereof that will engage the nut 124 during use. The threading 140 is threadedly engages the nut 124 mounted within the proximal portion 122 of the channel 120. The proximal end 138 of the set beam 136 of this embodiment includes a driving recess 144 configured to engage a driving tool used to rotate the set beam 136 relative to the nut 124 to adjust the position of the torque adjuster 114 along the cantilever beam 112.

Initially, the set beam 136 is rotated relative to the nut 124 and threaded within the proximal portion 122 of the channel 120 until the distal tip 110 is positioned in the space 117 between the first pair of adjacent teeth 116 of the gear cam 108. Thus, it will be understood by those of skill in the art that the desired torque limit may be at least partially controlled via a position of the set beam 136 relative to the body 102. In particular, the position of the set beam 136 relative to the body 102 determines a depth of the distal tip 110 within the space 117 between the adjacent teeth 116. However, as would be understood by those skilled in the art, in order for the markings on the torque wrench 100 to be accurate a user should insert the distal tip 110 fully into the space 117.

The cantilever beam 112 is constructed to have a bending stiffness selected such that, when the cantilever beam 112 is subject to a lateral force exceeding a predetermined force (i.e., a force applied by the first tooth 116A and the second tooth 116B defining the first space 117A as the body 102 is rotated relative thereto, the bending portion 113 of the cantilever beam 112 bends so that the distal tip 110 moves laterally along the second tooth 116B defining the first space 117A.

As described above, as the torque applied to the body 102 increases toward the set torque limit, the bending portion 113 bends until the distal tip 110 slips over the second tooth 116B into the second space 117B between the second tooth 116B and the third tooth 116C adjacent to the second tooth 116B. Thus, when the torque applied to the body 102 exceeds the pre-selected torque limit, the distal tip 110 slips from space 117 to space 117 (e.g., from the first space 117A to the second space 117B) without applying excessive torque to the body 102 and the fixation device, and the body 102 rotates about the central axis C relative to the gear cam 108. Although the exemplary embodiments show the cantilever beam 112 having a substantially circular cross-section, it will be understood by those of skill in the art, that the cantilever beam 112 may have any of a variety of geometries depending on the desired bending stiffness of the cantilever beam 112. The bending stiffness of the cantilever beam 112 may be determined via factors such as, for example, a length, shape, and/or diameter of the cantilever beam 112.

According to an exemplary embodiment, the torque adjuster 114 of the torque wrench 100 is configured as a slidable tab 142 that is slidable relative to both the body 102 and the cantilever beam 112 housed therein. A portion of the slidable tab 142 extends about the cantilever beam 112 to define the bending portion 113 of the cantilever beam 112. In particular, the slidable tab 142 engages the cantilever beam 112 so that a length of the cantilever beam 112 which extends distally of the torque adjuster 114 is unsupported laterally and thus defines a cantilevered bending portion 113 of the cantilever beam 112. The torque limit of the torque wrench 100 of this embodiment is adjusted by sliding the tab 142 longitudinally along the cantilever beam 112 relative to the body 102 to a position corresponding to the desired length of the bending portion 113 and, consequently, to a position corresponding to the desired torque limit. In a further embodiment, the body 102 includes markings therealong indicating torque limit settings corresponding to various positions of the tab 142/torque adjuster 114.

In one embodiment, the slidable tab 142 is biased toward a locked configuration via, for example, a biasing element such as a spring that urges the tab 142 into contact with a shoulder or other surface of the body 102 that prevents longitudinal movement of the tab 142. To unlock the slidable tab 142 so that the tab 142 may be slid longitudinally along the body 102, the user presses the tab 142 away from the shoulder or other surface to release the biasing element so that the tab 142 is slidable along the cantilever beam 112 and thus able to adjust the torque limit.

The user of the torque wrench 100 of this embodiment sets a desired torque limit for the torque wrench 100 based characteristics of a bone fixation device to be inserted and/or anatomical considerations, qualities of an implant to be affixed via the bone fixation device, etc. As described above, the desired torque limit using the torque wrench 100 of this embodiment is set by adjusting a position of the set beam 136 relative to the body 102 to control a degree of insertion of the distal tip 110 into the space 117 and/or by adjusting the position of the torque adjuster 114 relative to the body 102 by, for example, sliding the torque adjuster 114 relative to the body 102 to select a desired length of the bending portion 113. Upon setting the desired torque limit, the engaging portion 126 of the wrench head 104 is engaged with a fixation device such as a bone screw, nut, or bolt, etc., so that torsional force may be applied thereto via rotation of the torque wrench 100 relative to the fixation device.

As torque is applied, the teeth 116 of the gear cam 108 interface with the distal tip 110 to bend the bending portion 113 as the wrench head 104 rotates about the central axis C and the fixation device is, e.g., screwed into a bone and/or a bone fixation device such as a plate or other implant. The torque bends the bending portion 113 until, when the pre-set torque limit is reached, the distal tip 110 of the cantilever beam 112 slips from the space 117 between the pair of adjacent teeth 116 within which the distal tip 110 was positioned and the gear cam 108 rotates relative to the body 102 about the central axis C such that the distal tip 110 is subsequently received in an adjacent space 117 of the gear cam 108. Thus, at any time that the user attempts to exert a torsional force exceeding the set torque limit, the cantilever beam 112 will again bend so that the distal tip 110 similarly slips from the current space 117 within which it is lodged preventing the application to the fixation element of torque above the preset torque limit.

Figure 4:
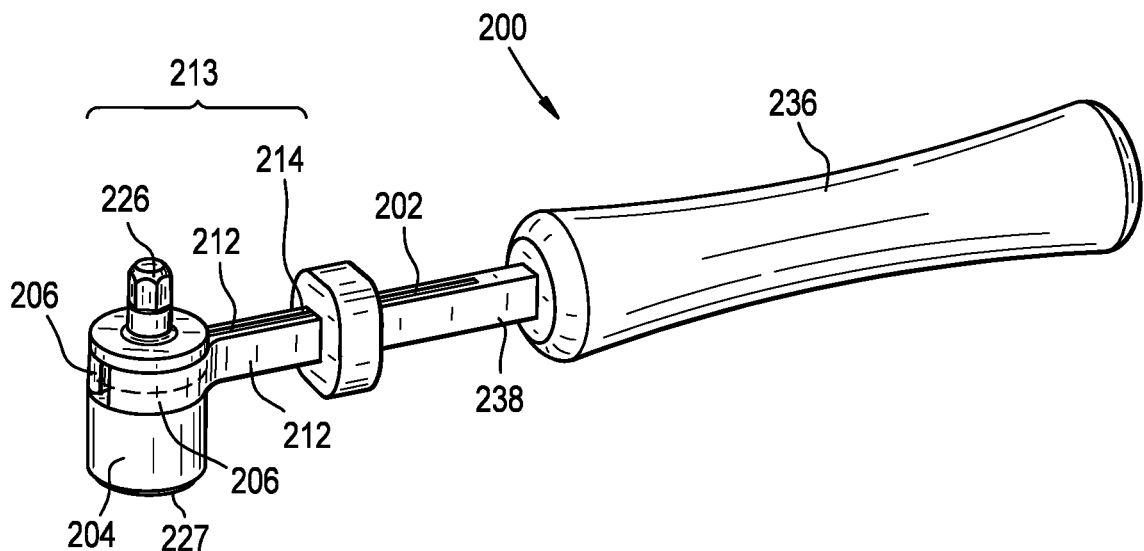
FIG. 4 shows a perspective view of a torque wrench according to another exemplary embodiment of the present disclosure.

As shown in FIGS. 4-8, a torque wrench 200 for applying a limited torsional force to a bone fixation device according to another exemplary embodiment of the present disclosure is substantially similar to the torque wrench 100, described above except as noted below. The torque wrench 200, as shown in FIG. 4, comprises a shaft 202 which acts as a cantilever and non-rotatably engages a wrench head 204 (for levels of torque below a selected torque limit) in a manner similar to that described above in regard to the torque wrench 100.

The torque wrench 200 similarly includes a torque adjuster 214 for adjusting a torque limit, as desired. The shaft 202 in this embodiment is split longitudinally along a length thereof to define a pair of arms 212 distal ends 206 of which are separated from one another across a gap. The distal ends 206 of the arms 212 engage and receive a gear cam 208 of the wrench head 204 therebetween, as will be described in further detail below. The torque wrench 200 further comprises a handle member 236 attached to a proximal end 238 of the shaft 202.

Figure 5:
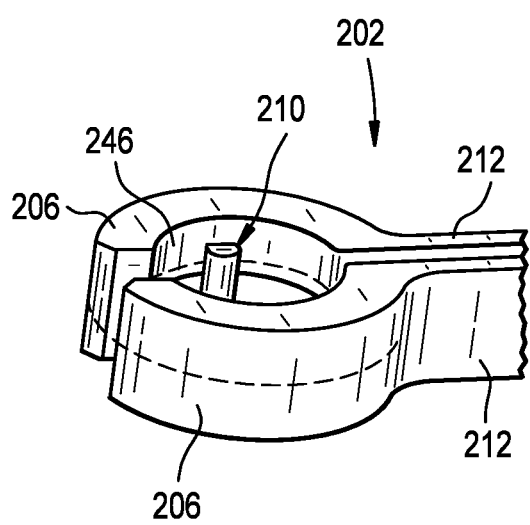
FIG. 5 shows a perspective view of a distal portion of a shaft according to the torque wrench of FIG. 4.

As described above, the shaft 202 is split to define two arms 212, the distal ends 206 of which are separated from one another. The distal ends 206 are sized, shaped, and biased to grippingly engage the gear cam 208 of the wrench head 204 therebetween so that the wrench head 204 is non-rotatable relative to the arms 212 for all levels of torque below a user selected torque limit. In an exemplary embodiment, as shown in FIG. 5, each of the distal ends 206 has a curved configuration shaped and sized to surround the wrench head 204 within curved interior surfaces 246 of the distal ends 206. Each of the distal ends 206 of this embodiment includes a protrusion 210 extending from the interior surfaces 246 toward a centerline of the shaft 202.

The protrusion 210 of each of the arms 212 is sized and shaped to received in a space extending between adjacent teeth 216 of the gear cam 208. In an exemplary embodiment, the protrusions 210 extend along the curved interior surfaces 246 to engage diametrically opposing portions of the gear cam 208. Those skilled in the art will recognize that any number of protrusions 210 may be included. For example, an embodiment having only one protrusion 210 on one of the arms 212 is possible as are embodiments including any number of protrusions on one or both of the arms 212.

The arms 212 of the shaft 202 are biased toward an engaging configuration in which each of the protrusions 210 is received within a space 217 between a respective pair of adjacent teeth 216 of the gear cam 208. As will be described in further detail below, each of the arms 206 has a bending stiffness selected such that, for a selected length of a bendable portion of the arms 212, the arms 212 will bend away from one another, increasing a distance between the distal ends 206 sufficient to permit the protrusions 210 to slip from the spaces 217 when a selected torque is applied to the gear cam 208 via the shaft 202. As the protrusions 210 slip from between the adjacent teeth 216, the wrench head 204 rotates about a central axis 2C thereof relative to the gear cam 208 so that no further torque beyond a set limit may be applied to the gear cam 208 and, consequently, to a fixation device received within the wrench head 204.

Figure 6:
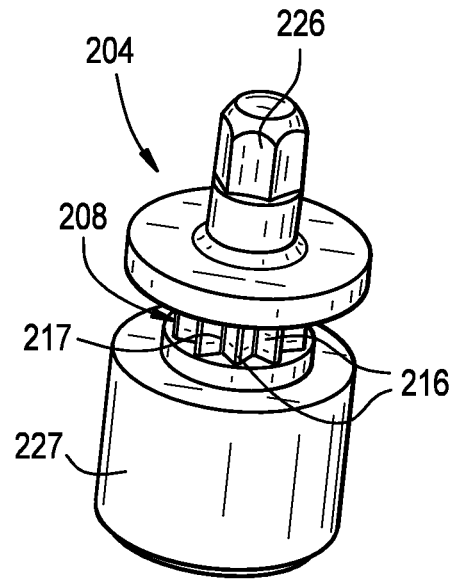
FIG. 6 shows a perspective view of a wrench head according to the torque wrench of FIG. 4.

As shown in FIG. 6, the wrench head 204 of this embodiment is similar to the wrench head 104, including the gear cam 208 formed on an outer circumference thereof and an inner circumferential engaging portion sized, shaped, and configured to non-rotatably engage a corresponding engaging portion of a fixation device (e.g., a head of a bone screw). The gear cam 208 is substantially similar to the gear cam 108 described above with respect to the torque wrench 100, including teeth 216 extending radially outward therefrom about an outer circumferential surface 232 and defining spaces 217 (e.g., a first space 217A, a second space 217B, a third space 217C and a fourth space 217D) between adjacent teeth 216 where the spaces 217 are sized and shaped to provisionally lock the protrusions 210 therein.

As discussed above, the gear cam 208 is rotatably received between the correspondingly curved interior surfaces 246 of the distal ends 206 of the arms 212 so that the wrench head 204 is rotatable relative to the shaft 202 about the central axis 2C depending on the torque required to bend the arms 212 sufficiently to permit each of the protrusions 210 to slip from one space 217 to another as will be described below.

In an exemplary embodiment, the wrench head 204 includes a first engaging portion 226 configured to engage a driving recess of a screw and a second engaging portion 227 configured as a socket including a recess sized, shaped, and configured to engage an exterior surface of a fixation device such as, for example, a bone screw, nut or bolt. The first and second engaging portions 226, 227 of this embodiment extend from diametrically opposed sides of the gear cam 208 so that each of the engaging portions 226, 227 protrudes from a surface of the corresponding distal end 206 configured to be couplable with a desired fixation device.

Although the wrench head 204 is shown and described as including two distinct engaging portions 226, 227, it will be understood by those of skill in the art that in some embodiments the wrench head 204 may include one of the engaging portions 226, 227. It will also be understood by those of skill in the art that although the torque wrench 100 is shown and described as including a single engaging portion 126, the torque wrench 100 may similarly include two engaging portions extending from opposing sides of the gear cam 108, as shown with respect to the wrench head 204.

As discussed above with respect to the torque wrench 100, a desired torque limit for the torque wrench 200 may be selected by manipulating geometric features of the torque wrench 200 such as, for example, a rigidity and/or a length of the arms 212 as well as by altering a length of a cantilevered bendable portion of the arms 212 as will be described below. Similarly to the torque wrench 100, the torque wrench 200 includes a torque adjuster 214 that is slidable along the shaft 202 to define a length of a bendable portion 213 (e.g., cantilever) of the shaft 202 extending from a distal end of the torque adjuster 214 to a distal end of the shaft 202.

As indicated above in regard to the torque wrench 100, the length of the bendable portion 213 of the shaft 202 determines a torque limit of the torque wrench 200 (i.e., a maximum torque that may be applied by the torque wrench 200 to a fixation device received therein). The torque adjuster 214 extends about and laterally restrains both of the arms 212, holding the arms 212 toward the biased configuration and preventing the portions of the arms 212 constituting the bendable portion 213 from being bent away from one another. Only portions of the arms 212 distal of the torque adjuster 214 (i.e., the portions of the arms 212 constituting the bendable portion 213) may be bent laterally outward relative to one another away from the biased position to permit movement of the protrusions 210 out of their current spaces 217. Thus, the position of the torque adjuster 214 longitudinally along the shaft 202 is altered by a user to select a desired torque limit in a manner similar to that described above in regard to the torque wrench 100.

The torque wrench 200 also includes the handle member 236 attached to the proximal end 238 of the shaft 202. The handle member 236 of this embodiment is ergonomically shaped to facilitate gripping by a user as would be understood by those skilled in the art. Although this exemplary embodiment shows the handle member 236 fixedly attached to the proximal end 238 of the shaft 202, in another embodiment, the handle member 236 may be longitudinally movable over the proximal end 238 so that the handle member 236 may be moved distally over a portion of the shaft 202 to adjust a torque limit—i.e., so that the torque adjuster 214 forms part of the handle member 236 and so that movement of the handle member 236 along the shaft 202 moves the torque adjuster 214 along the shaft 202 to select a desired torque limit. In such an embodiment, the bendable portion 213 may be defined as the portion of the shaft 202 extending distally from the handle member 236 or distally from a distal-most portion of the handle member 236 that laterally restrains the arms 212 in the same manner described above for the torque limiter 352.

In one embodiment, the handle member 236 is threadable over a proximal portion of the shaft 202. It will be understood by those of skill in the art, however, that the handle member 236 may be longitudinally slidable over the shaft 202 via or movable thereover via any of a number of mechanisms. It will also be understood by those of skill in the art that in embodiments in which the handle member 236 is movable over a length of the shaft 202, the torque wrench does not require a separate torque adjuster 214.

Figure 7:
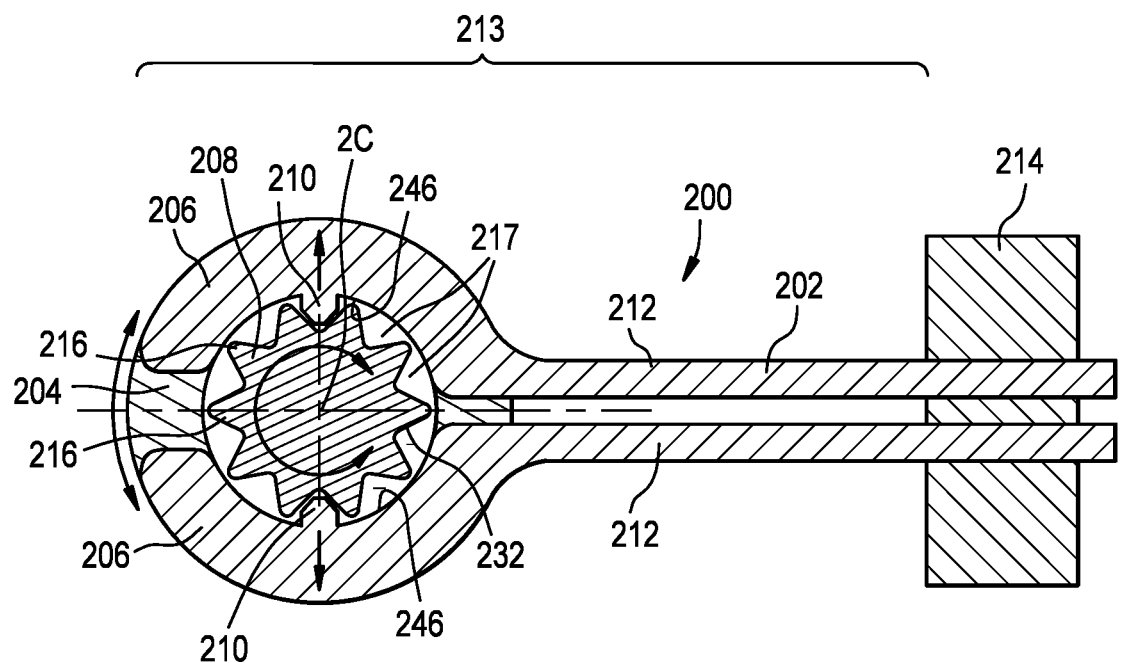
FIG. 7 shows a longitudinal-cross-sectional view of a distal portion of the torque wrench of FIG. 4.

According to an exemplary method using the torque wrench 200, the user selects a desired torque limit based on considerations similar to those described above (e.g., characteristics of a fixation device to be manipulated, a substance into which it is to be driven (e.g., a particular type of bone), etc. The desired torque limit is set by sliding the torque adjuster 214 longitudinally relative to the shaft 202 until a desired length of the bendable portion 213 is achieved, as shown in FIG. 7. Upon setting the desired torque limit, a fixation device is engaged to one of the engaging portions 226, 227 of the wrench head 204 so that the fixation device (e.g., screw, nut, bolt) may be driven into and/or fixed relative to a bone, as desired, by applying a torsional force thereto.

Figure 8:
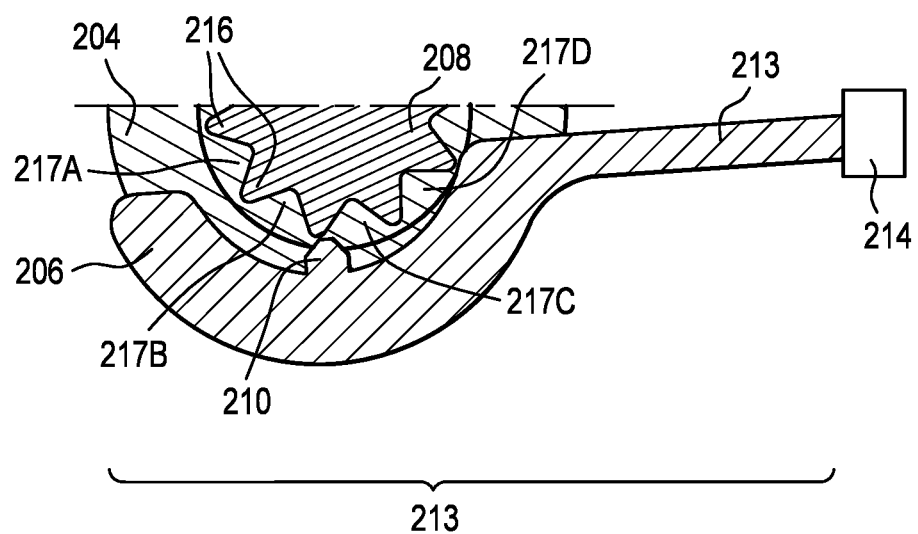
FIG. 8 shows a partial, longitudinal cross-sectional view of a distal portion of the torque wrench of FIG. 4.
Figure 9:
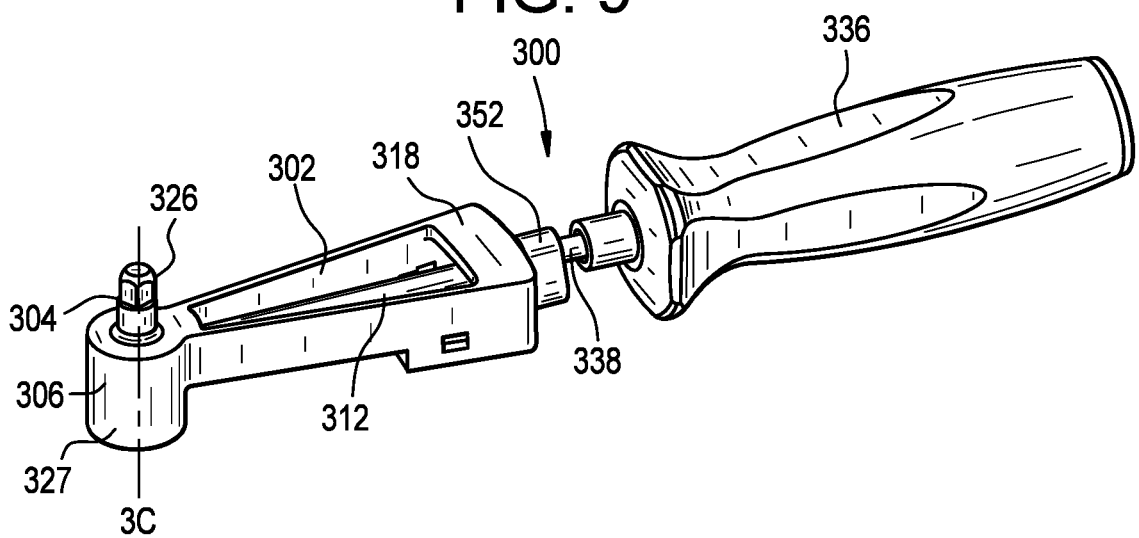
FIG. 9 shows a perspective view of a torque wrench according to yet another exemplary embodiment of the present disclosure.

When the desired torque limit has been reached, the force of the teeth 216 against the protrusions 210 bends the bendable portions 213 of the arms 212 to bend away from one another until the protrusions 210 slip out of their respective spaces 217 (e.g., the first space 217A and the second space 217B) and the gear cam 208 is permitted to rotate about the central axis 2C relative to the shaft 202 so that additional torque (i.e., torque in excess of the selected torque limit) is not applied to the fixation element, as shown in FIG. 8. The wrench head 204 continues to rotate until the distal ends 206 revert toward their biased configuration and the protrusions 210 are received within spaces 217 adjacent to the original spaces 217 (e.g., the third space 217C and the fourth space 217D adjacent to the first and second spaces 217A, B, respectively). Any torsional force exceeding the set torque limit will cause the protrusions 210 to continue to slip from the spaces 217 within which they are received so that no excessive torsional force may be applied to the bone fixation device.

As shown in FIGS. 9-14, a torque wrench 300 according to another exemplary embodiment is substantially similar to the torque wrenches 100, 200 described above except as described below. For example, the torque wrench 300 further comprises a torque indicator 350 which provides tactile feedback indicating to a user that a selected torque limit has been reached. Similarly to the torque wrench 100, the torque wrench 300, comprises a body 302 housing a wrench head 304 at a distal end 306 thereof and a shaft 312 extending proximally from the wrench head 304, within a channel 320 of the body 302. The torque indicator 350 is housed within a proximal end 322 of the channel 320 so that, when the shaft 312 is bent (e.g., rotated) beyond a selected torque limit, the torque indicator 350 interfaces with a torque limiter 352 positioned along the shaft 312 to provide tactile feedback to the user. Similarly to the torque wrench 200, the torque wrench 300 includes a handle member 336 attached to a proximal end 328 of the shaft 312.

The body 302 extends longitudinally from a proximal end 318 to the distal end 306 and includes the channel 320 extending therethrough. The channel 320 in this embodiment, tapers from the proximal end 318 toward the distal end 306 with the shaft 312 extending therethrough from a wider distal end to a narrow proximal end. The shaft 312 is movably mounted relative to the channel 320 so that the shaft may pivot about a central axis 3C of the wrench head 304 within the channel 320.

The wrench head 304 is rotatably mounted within the distal end 306 of the body 302, in communication with the channel 320, so that the wrench head 304 is rotatable about the central axis 3C, which extends substantially perpendicular to a longitudinal axis 3L of the body 302. The wrench head 304 of this embodiment, similarly to the wrench heads 104, 204, includes one or more engaging portions 326, 327 engaging corresponding engaging portions of a fixation device to which a torsional force is to be applied via the torque wrench 300. In one embodiment, a first engaging portion 326 is configured to engage driving recess of, for example, a screw while a second engaging portion 327 is configured as a socket including a recess sized, shaped, and configured to non-rotatably engage an exterior surface of an engaging portion of a fixation device such as, for example, the head of a bone screw, a nut or a bolt.

The shaft 312 extends longitudinally from a distal end 310 attached to the wrench head 304 to a proximal end 338 which may be attached to the handle member 336. As discussed above, the shaft 312 extends through the channel 320, with the proximal end 338 of the shaft 312 extending proximally of the proximal end 318 of the body 302 so that the handle member 336 extends proximally of the body 302. The handle members 336 of this embodiment is ergonomically shaped and configured to be gripped by a user providing a torsional force to the fixation device via the torque wrench 300.

The torque limiter 352 of this embodiment is configured as, for example, a ring 354, nut or other similarly configured element, which extends about the shaft 312, and a pair of protrusions 356 extending distally from a distal surface 355 of the ring 354, toward the distal end 306 of the body 302. The ring 354 is positioned along the shaft 312, immediately proximal of the proximal end 318 of the body 302, so that the protrusions 356 extend into the proximal end 322 of the channel 320.

In an exemplary embodiment, the protrusions 356 are configured as a pair of set screws driven distally through the ring 354 (e.g., moved distally and proximally within the ring 354 via rotation of the set screws and a, e.g., threaded connection between the ring 354 and the protrusions 356) through so that distal ends of the protrusions 356 extend distally from the distal surface 355. It will be understood by those of skill in the art, however, that the protrusions 356 may have any of a variety of configurations. The protrusions 356 extend distally from the distal surface 355 on opposing sides of the shaft 312 relative to one another to define a torque limit of the torque wrench 300 in either rotational direction.

The torque indicator 350 is coupled to an interior surface of the channel 320 at the proximal end 322 via a pin 366 so that the torque indicator 350 is rotatable about the pin 366. The torque indicator 350 extends along a side of the shaft 312 and is configured to interface with the torque limiter 352. According to an exemplary embodiment, extending proximally from the torque indicator 350 is a finger 358 that is sized, shaped, and configured to be received between the two protrusions 356 of the torque limiter 352.

Figure 10:
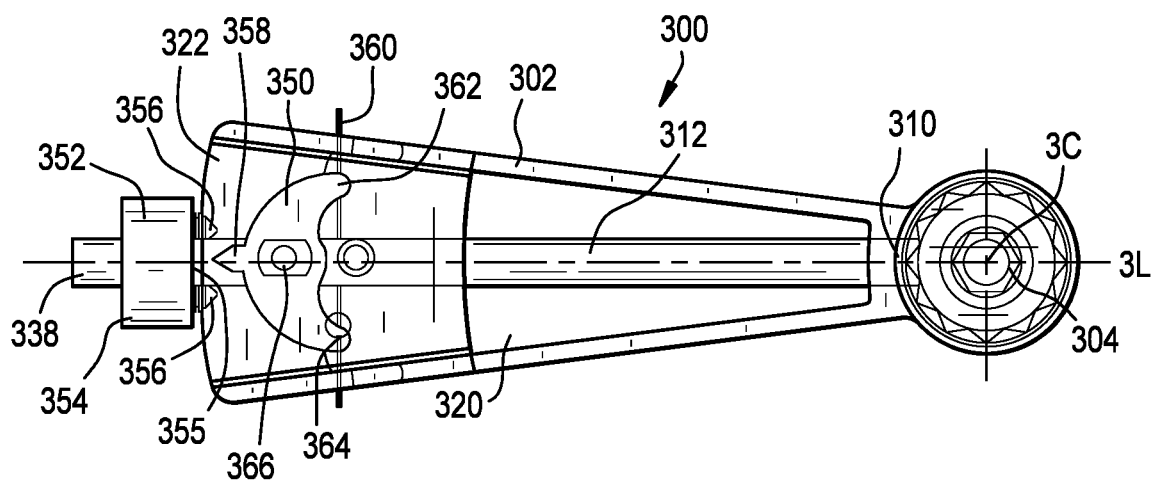
FIG. 10 shows a partially transparent side view of a distal portion of the torque wrench of FIG. 9.
Figure 11:
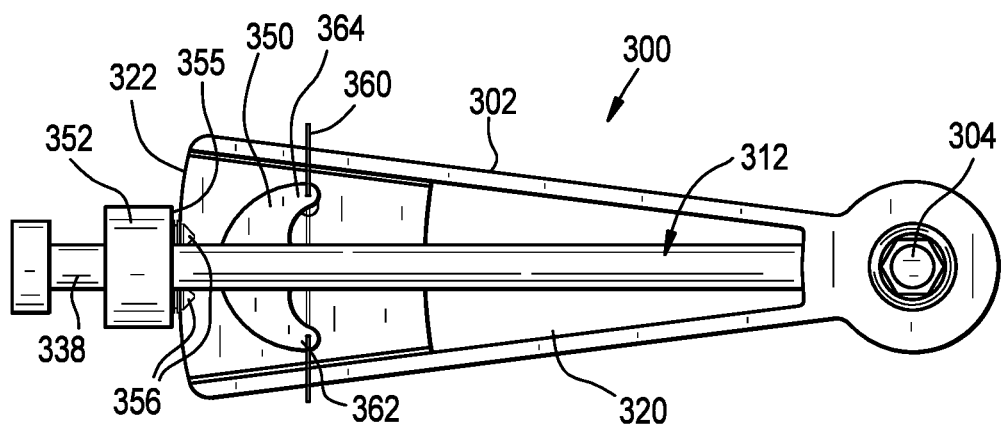
FIG. 11 shows another partially transparent side view of a distal portion of the torque wrench of FIG. 9.

According to an exemplary embodiment, the torque indicator 350 is biased toward a neutral position, as shown in FIGS. 10-11, in which the finger 358 is substantially centered between the two protrusions 356 of the torque limiter 352 (e.g., the finger 358 is aligned with the longitudinal axis 3L of the body 302). In an exemplary embodiment, the torque indicator 350 is biased toward this neutral position via a biasing element such as, for example, a torsion spring, extending across the channel 320, distally of the torque indicator 350. In this embodiment, the torque indicator 350 includes first and second wings 362, 364 which interface with opposing portions of the torsional spring 360 that bias the torque indicator 350 toward the neutral position.

Figure 12:
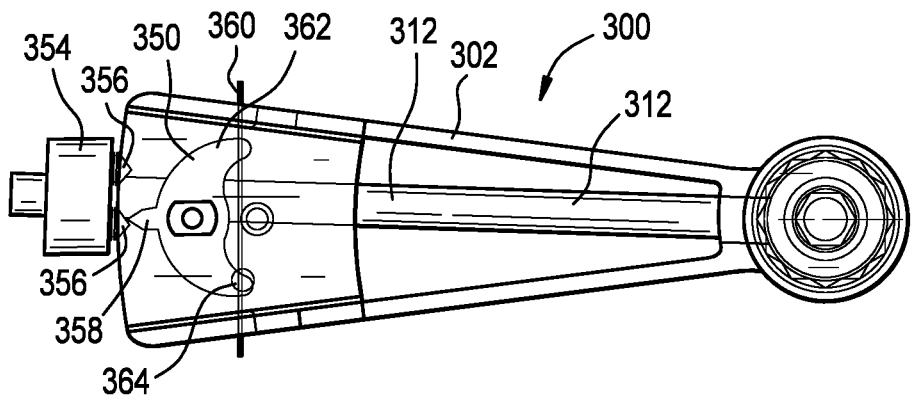
FIG. 12 shows a partially transparent side view of a distal portion of the torque wrench of FIG. 9, as a torsional force is being applied.
Figure 13:
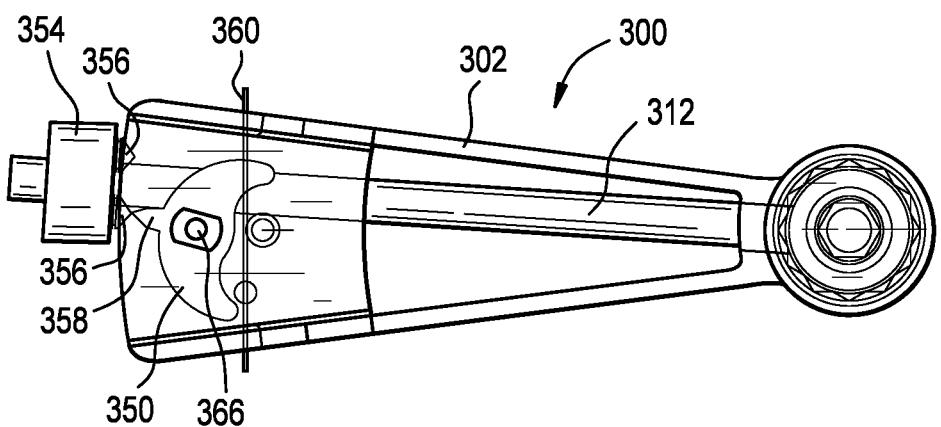
FIG. 13 shows a partially transparent side view of a distal portion of the torque wrench of FIG. 9, as a torque limit is being approached.
Figure 14:
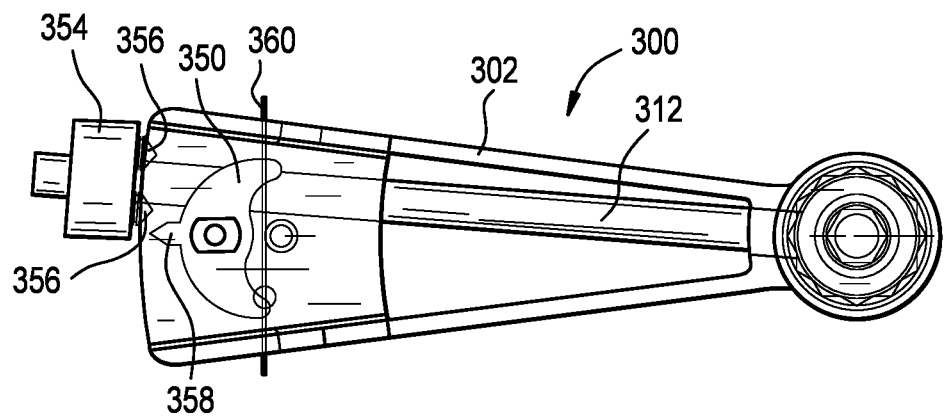
FIG. 14 shows a partially transparent side view of a distal portion of the torque wrench of FIG. 9, upon reaching a torque limit.

As torsional force is applied to a fixation device received within the torque wrench 300, the shaft 312 is bent relative to the central axis 3C of the wrench head 304 and the finger 358 of the torque indicator 350 abuts against one of the protrusions 356 of the torque limiter 352, as shown in FIG. 12. In other words, the shaft 312 is rotated relative to the central axis 3C so that the shaft 312 is angled with respect to the longitudinal axis 3L of the body 302. As the torque wrench 300 approaches a torque limit, as shown in FIG. 13, the torque indicator 350 begins to rotate about the pin 366 so that one of the first and second wings 362, 364 (depending on the rotational direction) is pressed against the torsion spring 360. When a torque limit provided by the torsion spring 360 is reached, the shaft 312 is sufficiently rotated so that the protrusion 356 is moved laterally past the finger 358, as shown in FIG. 14, a passing of the finger 358 over the protrusion 356 providing a tactile feedback to the user.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A torque wrench, comprising:
    an elongated body extending longitudinally from a proximal end to a distal end and including a channel extending therethrough, the distal end including an opening extending laterally therethrough along a central axis, the opening and the channel being in communication with one another;
    a wrench head rotatably received within the opening at the distal end of the elongated body so that the wrench head is rotatable about the central axis, the wrench head including a gear cam defining a plurality of teeth about a periphery thereof and an engaging portion sized, shaped, and configured to engage a corresponding engaging feature of a fixation device to which a torsional force is to be applied via the torque wrench;

a cantilever beam housed within the channel of the elongated body such that a distal tip thereof is received in a space between adjacent teeth of the gear cam, the cantilever beam configured to bend when a torsional force applied to the wrench head exceeds a predetermined torque limit so that the gear cam rotates about the central axis and the distal tip slips from the space between the teeth into an adjacent space;

a set beam extending proximally from a proximal end of the cantilever beam in longitudinal alignment therewith, the set beam configured to set the predetermined torque limit by engaging a proximal portion of the channel of the elongated body to fix a position of the cantilever beam within the elongated body and to control a degree of insertion of the distal tip into the space between adjacent teeth of the gear cam; and a torque adjuster extending about a portion of the cantilever beam and slidable along the elongated body to set a bendable length of the cantilever beam and adjust the predetermined torque limit of the torque wrench.

2. The torque wrench of claim 1, wherein the bendable length is defined via a portion of the cantilever beam extending distally of the torque adjuster.

3. The torque wrench of claim 1, wherein the torque adjuster is configured as a slidable tab biased toward a locked configuration, in which the tab is fixed in a position along the elongated body, and an unlocked configuration, in which the tab is slidable along the elongated body.

4. The torque wrench of claim 1, wherein the set beam includes a threading extending therealong.

5. The torque wrench of claim 4, further comprising a nut mounted within the proximal portion of the channel, the nut configured to threadedly engage the threading of the set beam.

6. A device for exerting a torsional force to a fixation device, comprising:

a body extending along a longitudinal axis from a proximal end to a distal end and including a channel extending therethrough along the longitudinal axis, the distal end including an opening extending laterally therethrough along a central axis;

a wrench head rotatably mounted within the opening such that the wrench head is rotatable about the central axis, the wrench head including a gear cam including teeth about a periphery thereof and an engaging portion configuration to engage a fixation device;

a cantilever beam extending through the channel so that a distal tip thereof is received between adjacent teeth of the gear cam, the cantilever beam configured to bend when a torsional force applied to the wrench head exceeds a predetermined torque limit so that the distal tip slips from between the adjacent teeth;

a set beam extending proximally from a proximal end of the cantilever beam in longitudinal alignment therewith, the set beam configured to set the predetermined torque limit by engaging a proximal portion of the channel of the body to fix a position of the cantilever beam within the body and to control a degree of insertion of the distal tip into a space between adjacent teeth of the gear cam; and a torque adjuster slidable along the body to set a desired bendable length of the cantilever beam and adjust the predetermined torque limit of the wrench head, the torque adjuster including a tab extending about a portion of the cantilever beam so that the tab is slidable along a length thereof.

7. The device of claim 6, wherein the tab is configured to be movable between a locked configuration, in which the tab is in a fixed position along the body, and an unlocked configuration, in which the tab is slidable along the body.

8. The device of claim 6, wherein the set beam includes a threading extending thereabout and along a length thereof.

9. The device of claim 8, wherein a proximal portion of the channel of the body includes a nut mounted therein, the nut configured to threadedly engage the set beam therein.

10. A method for applying a torsional force to a fixation device, comprising:

engaging an engaging element of a wrench head of a torque wrench with a corresponding engaging portion of the fixation device, the torque wrench including an elongated body, a gear cam of the wrench head rotatably mounted within an opening at a distal end of the elongated body, a cantilever beam extending through the elongated body so that a distal tip of the cantilever beam is received in a space between adjacent teeth of the gear cam, and a set beam extending proximally from a proximal end of the cantilever beam to control a degree of insertion of the distal tip into the space between adjacent teeth of the gear cam;

adjusting a torque limit of the torque wrench by sliding a torque adjuster along a length of the elongated body and the cantilever beam to define a bendable length of the cantilever beam; and applying a torsional force to the fixation device by rotating the elongated body about a central axis of the wrench head until the torque limit is reached, wherein, when the torque limit is reached, the cantilever beam bends such that the gear cam rotates about the central axis and the distal tip of the cantilever beam slips from between the adjacent teeth so that no further torsional force is applied to the fixation device.

11. The method of claim 10, wherein the torque limit is adjusted by adjusting a position of the cantilever beam relative to the elongated body by fixing the set beam relative to the elongated body.

12. The method of claim 10, wherein a proximal portion of the elongated body includes a nut mounted therein and the set beam includes a threading extending therealong for threadedly engaging the nut.

* * * * *